US007029896B2

(12) United States Patent
Suga et al.

(10) Patent No.: US 7,029,896 B2
(45) Date of Patent: Apr. 18, 2006

(54) PHOSPHOSERINE PHOSPHATASE GENE OF CORYNEFORM BACTERIA

(75) Inventors: Mikiko Suga, Kawasaki (JP); Yoko Asakura, Kawasaki (JP); Masakazu Sugimoto, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/321,382

(22) Filed: Dec. 18, 2002

(65) Prior Publication Data
US 2003/0114656 A1 Jun. 19, 2003

Related U.S. Application Data

(63) Continuation of application No. 10/081,859, filed on Feb. 25, 2002, now abandoned, and a continuation of application No. 09/761,716, filed on Jan. 18, 2001, now Pat. No. 6,395,528.

(30) Foreign Application Priority Data

Jan. 27, 2000 (JP) ............................... 2000-23341

(51) Int. Cl.
C12N 9/16 (2006.01)
C12N 1/20 (2006.01)
C12P 13/16 (2006.01)
C12P 21/04 (2006.01)
C07H 21/04 (2006.01)

(52) U.S. Cl. ..................... 435/196; 435/116; 435/4; 435/6; 435/252.3; 435/320.1; 435/69.1; 435/71.1; 536/23.1; 536/23.2; 536/23.7

(58) Field of Classification Search ................ 435/116, 435/196, 252.3, 320.1, 71.1, 440, 6, 4, 69.1; 536/23.2, 23.7, 23.1
See application file for complete search history.

(56) References Cited

U.S. PATENT DOCUMENTS 4,965,197 A 10/1990 Liebl et al.
6,037,154 A 3/2000 Suga et al.

FOREIGN PATENT DOCUMENTS

EP 0 943 687 2/1999
EP 0 931 833 7/1999
WO WO 01/00843 1/2001
WO WO 01/064899 9/2001

OTHER PUBLICATIONS

A. F. Neuwald et al., Nucle.c Acids Res. GenBank X03046 vol. 13, No. 19, 3 pages "DNA Sequence and Characterization of the *Escherichia coli* serB Gene." 1985 (Abstract Only).
A.F. Neuwald et al., Gene, Genbank M30784, vol. 82, 2 pages "An *Escherichia coli* Membrane Protein with a Unique Signal Sequence," 1989 (Abstract Only).

J. M. Song, et al., Dept. of Molecular and Cell Biology, University of California, Unpublished, GenBank U36473, 2 pages, "Identification and Characterization of the *Saccharomyces cerevisiae* SER2 Gene," Sep. 18, 1995 (Abstract Only).
S. L. Martin et al., J. Biol. Chem., GenBank AF006039, vol. 272, No. 34, 3 pages, "Lewis X Biosynthesis on *Helicobacter pylor*. Molecular Cloning of an Alpha (1,3)-Fucosyltransferase Gene," 1997 (Abstract Only).
S.T. Cole et al., "Deciphering the Biology of Micobacterium Tuberculosis from the Complete Genome Sequence", Nature, vol. 396, Nov. 12, 1998, pp. 537-544.
Cole et al., Pir Database—Accession #E70860, 1998.
U.S. Appl. No. 09/577,005, filed May 25, 2000, Asakura et al.
U.S. Appl. No. 09/835,381, filed Apr. 17, 2001, Suga et al.
U.S. Appl. No. 10/009,777, filed Dec. 17, 2001, Sugimoto et al.
U.S. Appl. No. 10/019,284, filed Jan. 2, 2002, Sugimoto et al.
U.S. Appl. No. 10/148,898, filed Jun. 19, 2002, Sugimoto et al.
A. F. Neuwald, et al., Database EMBL, AN X03046, pp. 1-3, XP-002280924, "E. coli Phosphoserine Phosphatase (SERB) and SMP Protein Genes", Jan. 28, 1986.
A. F. Neuwald, et al., Nucleic Acids Research, vol. 13, No. 19, pp. 7025-7039, XP-002280923, "DNA Sequence and Characterization of the *Escherichia coli* SERB Gene", Oct. 11, 1985.
H. Yoshida, et al., Nippon Nogie Kagakukaishi-Journal of the Agricultural Chemical Society of Japan, vol. 48, pp. 201-208, XP-008030518, "Production of L-Serine by L-Serine Analog-Resistant Mutants from Various Bacteria and the Effect of L-Threonine and L-Homoserine on the Production of L-Serine (Fermentation Production of L-Serine III)", 1974.

*Primary Examiner*—Manjunath Rao
*Assistant Examiner*—Yong Pak
(74) *Attorney, Agent, or Firm*—Oblon, Spivak, McClelland, Maier & Neustadt, P.C.

(57) ABSTRACT

The present invention provides a DNA coding for a protein defined in the following (A) or (B) is obtained from *Brevibacterium flavum* chromosomal DNA library by cloning a DNA fragment that complicates serB deficiency of *Escherichia coli* as a open reading frame in the DNA fragment.

(A) A protein which comprises an amino acid sequence of SEQ ID: 2 in Sequence Listing; or (B) A protein which comprises an amino acid sequence including substitution, deletion, insertion, addition or inversion of one or several amino acids in the amino acid sequence of SEQ ID NO: 2 in Sequence Listing, and which has phosphoserine phosphatase activity.

4 Claims, No Drawings

SEQUENCE LISTING

<160> NUMBER OF SEQ ID NOS: 4

<210> SEQ ID NO 1
<211> LENGTH: 1875
<212> TYPE: DNA
<213> ORGANISM: Brevibacterium flavum
<220> FEATURE:
<221> NAME/KEY: CDS
<222> LOCATION: (210)..(1547)

<400> SEQUENCE: 1

```
gaattcggta ccgcccagcc cttgcatctg actccagtcg ctaaaagcgt ctgatttaag      60
tcggtacctg actaaataag caccagcccc agcagagata atctgccggg gctggtgctt     120
ttcatattcc gacttggggc acccctgaat acatctcacc caatccccca aagctacaca     180
attgtccagc aacgactgat aaatctcca atg tcg tgt tcc gcg ctc aga cat        233
                                  Met Ser Cys Ser Ala Leu Arg His
                                  1               5 gag aca att gtt gcc gtg act gaa ctc atc cag aat gaa tcc caa gaa        281
Glu Thr Ile Val Ala Val Thr Glu Leu Ile Gln Asn Glu Ser Gln Glu
    10              15                  20 atc gct gag ctg gaa gcc gga cag cag gtt gca ttg cgt gaa ggt tat        329
Ile Ala Glu Leu Glu Ala Gly Gln Gln Val Ala Leu Arg Glu Gly Tyr
25              30                  35                  40 ctt cct gcg gtg atc aca gtg agc ggt aaa gac cgc cca ggt gtg act        377
Leu Pro Ala Val Ile Thr Val Ser Gly Lys Asp Arg Pro Gly Val Thr
                45                  50                  55 gcc gcg ttc ttt agg gtc ttg tcc gct aat cag gtt cag gtc ttg gac        425
Ala Ala Phe Phe Arg Val Leu Ser Ala Asn Gln Val Gln Val Leu Asp
            60                  65                  70 gtt gag cag tca atg ttc cgt ggc ttt ttg aac ttg gcg gcg ttt gtg        473
Val Glu Gln Ser Met Phe Arg Gly Phe Leu Asn Leu Ala Ala Phe Val
        75                  80                  85 ggt atc gca cct gag cgt gtc gag acc gtc acc aca ggc ctg act gac        521
Gly Ile Ala Pro Glu Arg Val Glu Thr Val Thr Thr Gly Leu Thr Asp
    90                  95                  100 acc ctc aag gtg cat gga cag tcc gtg gtg gtg gag ctg cag gaa act        569
Thr Leu Lys Val His Gly Gln Ser Val Val Val Glu Leu Gln Glu Thr
105                 110                 115                 120 gtg cag tcg tcc cgt cct cgt tct tcc cat gtt gtt gtg gtg ttg ggg        617
Val Gln Ser Ser Arg Pro Arg Ser Ser His Val Val Val Val Leu Gly
                125                 130                 135 gat ccg gtt gat gcg ttg gat att tcc cgc att ggt cag acc ctg gcg        665
Asp Pro Val Asp Ala Leu Asp Ile Ser Arg Ile Gly Gln Thr Leu Ala
            140                 145                 150 gat tac gat gcc aac att gac acc att cgt ggt att tcg gat tac cct        713
Asp Tyr Asp Ala Asn Ile Asp Thr Ile Arg Gly Ile Ser Asp Tyr Pro
        155                 160                 165 gtg acc ggc ctg gag ctg aag gtg act gtg ccg gat gtc agc cct ggt        761
Val Thr Gly Leu Glu Leu Lys Val Thr Val Pro Asp Val Ser Pro Gly
    170                 175                 180 ggt ggt gaa gcg atg cgt aag gcg ctt gct gct ctt acc tct gag ctg        809
Gly Gly Glu Ala Met Arg Lys Ala Leu Ala Ala Leu Thr Ser Glu Leu
185                 190                 195                 200 aat gtg gat att gcg att gag cgt tct ggt ttg ctg cgt cgt tct aag        857
Asn Val Asp Ile Ala Ile Glu Arg Ser Gly Leu Leu Arg Arg Ser Lys
```

```
cgt ctg gtg tgc ttc gat tgt gat tcc acg ttg atc act ggt gag gtc      905
Arg Leu Val Cys Phe Asp Cys Asp Ser Thr Leu Ile Thr Gly Glu Val
        220                 225                 230 att gag atg ttg gcg gct cac gcg ggc aag gaa gct gaa gtt gcg gca      953
Ile Glu Met Leu Ala Ala His Ala Gly Lys Glu Ala Glu Val Ala Ala
            235                 240                 245 gtt act gag cgt gcg atg cgc ggt gag ctc gat ttc gag gag tct ctg     1001
Val Thr Glu Arg Ala Met Arg Gly Glu Leu Asp Phe Glu Glu Ser Leu
    250                 255                 260 cgt gag cgt gtg aag gcg ttg gct ggt ttg gat gcg tcg gtg atc gat     1049
Arg Glu Arg Val Lys Ala Leu Ala Gly Leu Asp Ala Ser Val Ile Asp
265                 270                 275                 280 gag gtc gct gcc gct att gag ctg acc cct ggt gcg cgc acc acg atc     1097
Glu Val Ala Ala Ala Ile Glu Leu Thr Pro Gly Ala Arg Thr Thr Ile
                285                 290                 295 cgt acg ctg aac cgc atg ggt tac cag acc gct gtt gtt tcc ggt ggt     1145
Arg Thr Leu Asn Arg Met Gly Tyr Gln Thr Ala Val Val Ser Gly Gly
            300                 305                 310 ttc atc cag gtg ttg gaa ggt ttg gct gag gag ttg gag ttg gat tat     1193
Phe Ile Gln Val Leu Glu Gly Leu Ala Glu Glu Leu Glu Leu Asp Tyr
        315                 320                 325 gtc cgc gcc aac act ttg gaa atc gtt gat ggc aag ctg acc ggc aac     1241
Val Arg Ala Asn Thr Leu Glu Ile Val Asp Gly Lys Leu Thr Gly Asn
330                 335                 340 gtc acc ggc aag atc gtt gac cgc gct gcg aag gct gag ttc ctc cgt     1289
Val Thr Gly Lys Ile Val Asp Arg Ala Ala Lys Ala Glu Phe Leu Arg
345                 350                 355                 360 gag ttc gct gcg gat tct ggc ctg aag atg tac cag act gtc gct gtc     1337
Glu Phe Ala Ala Asp Ser Gly Leu Lys Met Tyr Gln Thr Val Ala Val
                365                 370                 375 ggt gat ggc gct aat gac atc gat atg ctc tcc gct gcg ggt ctg ggt     1385
Gly Asp Gly Ala Asn Asp Ile Asp Met Leu Ser Ala Ala Gly Leu Gly
            380                 385                 390 gtt gct ttc aac gcg aag cct gcg ctg aag gag att gcg gat act tcc     1433
Val Ala Phe Asn Ala Lys Pro Ala Leu Lys Glu Ile Ala Asp Thr Ser
        395                 400                 405 gtg aac cac cca ttc ctc gac gag gtt ttg cac atc atg ggc att tcc     1481
Val Asn His Pro Phe Leu Asp Glu Val Leu His Ile Met Gly Ile Ser
410                 415                 420 cgc gac gag atc gat ctg gcg gat cag gaa gac ggc acc ttc cac cgc     1529
Arg Asp Glu Ile Asp Leu Ala Asp Gln Glu Asp Gly Thr Phe His Arg
425                 430                 435                 440 gtt cca ttg acc aat gcc taaagattcg cttctcgacg cccacctcct            1577
Val Pro Leu Thr Asn Ala
                445 cctcaaggcc cgggctagcg acgggccaca tagcgaggat ccttcggatc cttcgaccgt   1637 tcaggcaatg cagatcgcgt tgcacattcc gaaacagaat ccgccccggc ggacagatgt   1697 gttggaagcg gcggcgagga gtgtggtcaa gctttgcctc gacgaacgag tatccaccga   1757 tcctgatttt cgggcggcct tggaacgttg gtacggacac ttgattcgga aggtgtcacg   1817 tcgcgctcgt aatgcggcgt gggatcgggt gcaagattta cccggcgtga ctgtcgac    1875
```

<210> SEQ ID NO 2
<211> LENGTH: 446
<212> TYPE: PRT
<213> ORGANISM: Brevibacterium flavum

<400> SEQUENCE: 2

-continued

```
Met Ser Cys Ser Ala Leu Arg His Glu Thr Ile Val Ala Val Thr Glu
1               5                   10                  15

Leu Ile Gln Asn Glu Ser Gln Glu Ile Ala Glu Leu Glu Ala Gly Gln
                20                  25                  30

Gln Val Ala Leu Arg Glu Gly Tyr Leu Pro Ala Val Ile Thr Val Ser
            35                  40                  45

Gly Lys Asp Arg Pro Gly Val Thr Ala Ala Phe Phe Arg Val Leu Ser
    50                  55                  60

Ala Asn Gln Val Gln Val Leu Asp Val Glu Gln Ser Met Phe Arg Gly
65                  70                  75                  80

Phe Leu Asn Leu Ala Ala Phe Val Gly Ile Ala Pro Glu Arg Val Glu
                85                  90                  95

Thr Val Thr Thr Gly Leu Thr Asp Thr Leu Lys Val His Gly Gln Ser
            100                 105                 110

Val Val Val Glu Leu Gln Glu Thr Val Gln Ser Ser Arg Pro Arg Ser
        115                 120                 125

Ser His Val Val Val Leu Gly Asp Pro Val Asp Ala Leu Asp Ile
    130                 135                 140

Ser Arg Ile Gly Gln Thr Leu Ala Asp Tyr Asp Ala Asn Ile Asp Thr
145                 150                 155                 160

Ile Arg Gly Ile Ser Asp Tyr Pro Val Thr Gly Leu Glu Leu Lys Val
                165                 170                 175

Thr Val Pro Asp Val Ser Pro Gly Gly Gly Glu Ala Met Arg Lys Ala
            180                 185                 190

Leu Ala Ala Leu Thr Ser Glu Leu Asn Val Asp Ile Ala Ile Glu Arg
        195                 200                 205

Ser Gly Leu Leu Arg Arg Ser Lys Arg Leu Val Cys Phe Asp Cys Asp
    210                 215                 220

Ser Thr Leu Ile Thr Gly Glu Val Ile Glu Met Leu Ala Ala His Ala
225                 230                 235                 240

Gly Lys Glu Ala Glu Val Ala Ala Val Thr Glu Arg Ala Met Arg Gly
                245                 250                 255

Glu Leu Asp Phe Glu Glu Ser Leu Arg Glu Arg Val Lys Ala Leu Ala
            260                 265                 270

Gly Leu Asp Ala Ser Val Ile Asp Glu Val Ala Ala Ile Glu Leu
        275                 280                 285

Thr Pro Gly Ala Arg Thr Thr Ile Arg Thr Leu Asn Arg Met Gly Tyr
    290                 295                 300

Gln Thr Ala Val Val Ser Gly Gly Phe Ile Gln Val Leu Glu Gly Leu
305                 310                 315                 320

Ala Glu Glu Leu Glu Leu Asp Tyr Val Arg Ala Asn Thr Leu Glu Ile
                325                 330                 335

Val Asp Gly Lys Leu Thr Gly Asn Val Thr Gly Lys Ile Val Asp Arg
            340                 345                 350

Ala Ala Lys Ala Glu Phe Leu Arg Glu Phe Ala Asp Ser Gly Leu
        355                 360                 365

Lys Met Tyr Gln Thr Val Ala Val Gly Asp Gly Ala Asn Asp Ile Asp
    370                 375                 380

Met Leu Ser Ala Ala Gly Leu Gly Val Ala Phe Asn Ala Lys Pro Ala
385                 390                 395                 400

Leu Lys Glu Ile Ala Asp Thr Ser Val Asn His Pro Phe Leu Asp Glu
                405                 410                 415
```

-continued

```
Val Leu His Ile Met Gly Ile Ser Arg Asp Glu Ile Asp Leu Ala Asp
            420             425             430

Gln Glu Asp Gly Thr Phe His Arg Val Pro Leu Thr Asn Ala
        435             440             445

<210> SEQ ID NO 3
<211> LENGTH: 36
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 3
gctccagaat tcggtaccgc ccagcccttg catctg                                36

<210> SEQ ID NO 4
<211> LENGTH: 36
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 4
catcgtcgac agtcacgccg ggtaaatctt gcaccc                                36
```

US 7,029,896 B2

PHOSPHOSERINE PHOSPHATASE GENE OF CORYNEFORM BACTERIA

This application is a Continuation of U.S. application Ser. No. 10/081,859, filed on Feb. 25, 2002 now abandoned, which is a Continuation of U.S. application Ser. No. 09/761,716, filed on Jan. 18, 2001, now U.S. Pat. No. 6,395,528.

BACKGROUND OF THE INVENTION

1. Field of the Invention

The present invention relates to the DNA coding for phosphoserine phosphatase of coryneform bacteria. The DNA may be utilized for microbiologic industry, such as breeding L-serine producing coryneform bacteria.

2. Description of the Related Art

As a conventional method of producing L-serine by fermentation, there has been reported the method in which a bacterial strain capable of converting glycine and sugar into L-serine is used in a medium containing 30 g/L of glycine to produce at most 14 g/L of L-serine. The conversion yield amounted to 46% (Kubota, K., *Agricultural Biological Chemistry*, 49, 7–12 (1985)). Using a bacterial strain capable of converting glycine and methanol into L-serine, 53 g/L of L-serine can be produced from 100 g/L of glycine (T. Yoshida et al., *Journal of Fermentation and Bioengineering*, Vol. 79, No. 2, 181–183, 1995). In the method using Nocardia, it has been known that the L-serine productivity of the bacterium can be improved by breeding those strains resistant to serine hydroxamate, azaserine or the like (Japanese Patent Publication No. 57-1235). However, these methods involve use of glycine that is a precursor of L-serine and include complicated operation and is disadvantageous from the viewpoint of costs.

As strains that can ferment L-serine directly from a sugar and do not need addition of the precursor of L-serine to the medium, there has been known *Corynebacterium glutamicum* that is resistant to D-serine, á-methylserine, o-methylserine, isoserine, serine hydroxamate, and 3-chloroalanine but the accumulation of L-serine is as low as 0.8 g/L (*Nogei Kagakukaishi*, Vol. 48, No. 3, p. 201–208, 1974). Accordingly, further strain improvements are needed for direct fermentation of L-serine on an industrial scale.

On the other hand, regarding coryneform bacteria, there have been disclosed a vector plasmid that is capable of autonomous replication in the cell and having a drug resistance marker gene (cf. U.S. Pat. No. 4,514,502) and a method of introducing a gene into the cell (Japanese Patent Application Laid-open No. 2-207791). These techniques have been utilized for breeding L-amino acid producing bacteria. As for L-serine, it has been found that L-serine productivity of coryneform bacteria having the L-serine producing ability is improved by introduction of a gene coding for D-3-phosphoglyceratehydrogenase whose feedback inhibition by L-serine is desensitized (serA gene) (European Patent Application Laid-Open No. 943687), or amplification of a gene coding for phosphoserine phosphatase (serB) or phosphoserine transaminase (serC) (European Patent Application Laid-Open No. 931833). There has been known serB gene in *Escherichia coli* (GenBank accession X03046, M30784), Yeast. (GenBank accession U36473), *Helicobacter pylori* (GenBank accession AF006039), however, serB gene of coryneform bacteria has not been known.

SUMMARY OF THE INVENTION

An object of the present invention, in view of the aforementioned points, is to provide the DNA coding for phosphoserine phosphatase of coryneform bacteria.

The present inventors obtained the DNA fragment from a chromosome DNA library of *Brevibacterium flavum*, which complimented serB deficiency of *Escherichia coli*. The open reading frame having homology with known serB gene of *Escherichia coli* was subcloned from the DNA fragment and introduced into serB deficient mutant strain of aforementioned *Escherichia coli*. However, serB deficiency was not complemented. It was found that serB deficiency was complemented with the aforementioned ORF which was forcedly expressed utilizing lac promoter. Thus, it was confirmed that the aforementioned ORF was serB homologue of *Brevibacterium flavum*. It was indicated that the aforementioned ORF did not have its own promoter because of forming operon.

The present invention was accomplished as described above, and provides the followings.

(1) A protein defined in the following (A) or (B):
(A) A protein which comprises an amino acid sequence of SEQ ID: 2 in Sequence Listing; or
(B) A protein which comprises an amino acid sequence including substitution, deletion, insertion, addition or inversion of one or several amino acids in the amino acid sequence of SEQ ID NO: 2 in Sequence Listing, and which has phosphoserine phosphatase activity.

(2) A DNA coding for a protein as defined in the following (A) or (B):
(A) A protein which comprises an amino acid sequence of SEQ ID: 2 in Sequence Listing; or
(B) A protein which comprises an amino acid sequence including substitution, deletion, insertion, addition or inversion of one or several amino acids in the amino acid sequence of SEQ ID NO: 2 in Sequence Listing, and which has phosphoserine phosphatase activity.

(3) A DNA coding for a protein having phosphoserine phosphatase activity, which hybridizes under stringent conditions to a DNA sequence encoding a protein which comprises an amino acid sequence of SEQ ID NO: 2.

(4) The DNA according to (3), the stringent conditions comprise washing at 60° C. and at a salt concentration corresponding to 1×SSC and 0.1% SDS.

(5) The DNA according to (2), which is DNA as defined in the following (a) or (b):
(a) A DNA which comprises a nucleotide sequence corresponding to nucleotide numbers of 210–1547 of nucleotide sequence of SEQ NO: 1 in Sequence Listing; or
(b) A DNA which is hybridizable with a probe which comprises the nucleotide sequence corresponding to nucleotide numbers of 210–1547 of nucleotide sequence of SEQ NO: 13 in Sequence Listing or a partial nucleotide sequence under stringent conditions, and which codes for the protein having the phosphoserine phosphatase activity.

(6) The DNA according to (5), the stringent conditions comprise washing at 60° C. and at a salt concentration corresponding to 1×SSC and 0.1% SDS.

(7) A vector comprising the DNA according to any of (1) to (6).

(8) A bacterial cell in which phosphoserine phosphatase activity encoded by the DNA according to any of (1) to (16) is increased.

(9) A method of producing L-serine comprising the steps of cultivating the bacterium according to (8) in a medium to produce and accumulate L-serine in the medium, and collecting L-serine from the medium.

Hereafter, the present invention will be explained in detail.

The DNA of the present invention can be obtained through PCR (polymerase chain reaction) utilizing chromosomal DNA of *Brevibacterium flavum,* for example, the *Brevibacterium flavum* strain ATCC14067, as a template, as well as a primer having the nucleotide sequence of SEQ ID NOs: 3 and 4 shown in sequence listing. Because each of these primers has a restriction enzyme recognition site of EcoRI or SalI in their 5' sequences, the amplification product digested with these restriction enzymes can be inserted into a vector having EcoRI and SalI digested ends.

The nucleotide sequences of the aforementioned primers were designed based on the nucleotide sequence of the DNA fragment which complements serB deficient mutant strain *Escherichia coli* ME8320 (thi, serB, zhi-1::Tn10) (available from national genetics institute). By using these primers, a DNA fragment containing the coding region of the serB homologue and its flanking region (5' non-translation region of about 200 bp and 3' non-translation region of about 300 bp) can be obtained.

The nucleotide sequence of the coding region of the DNA of the present invention obtained as described above and an amino acid sequence which may be encoded by the sequence are shown in SEQ ID NO: 1. The amino acid sequence alone is shown in SEQ ID NO: 2.

The aforementioned serB homologue was found as the open reading frame (ORF) having homology with serB genes of *Escherichia coli* and Yeast (*Saccharomyces cerevisiae*), which existed in the DNA fragment complementing serB deficiency of strain ME8320. The DNA fragment having enough length to contain the ORF and the promoter was obtained from *Brevibacterium flavum* ATCC14067 by PCR utilizing aforementioned primers having the nucleotide sequence of SEQ ID NOs: 3 and 4 shown in sequence listing. It was introduced into strain ME8320, however the serB deficiency of the strain was not complemented. Therefore, at first, it was thought that the aforementioned ORF was not serB homologue. However, the serB deficiency was complemented with the aforementioned ORF which was ligated to lac promoter and forcedly expressed. Thus, it was confirmed that the aforementioned ORF was serB homologue.

Further, the other ORF was found just upstream of serB homologue in the DNA fragment that compliments serB deficiency. From these results, it was indicated that these ORFs form a operon and there was no promoter region and the like just upstream of serB homologue.

At first, it was attempted to obtain serB homologue of *Brevibacterium flavum* utilizing nucleotide sequence of known serB gene. That is, the inventors intended to compare nucleotide sequence and amino acid sequence of known serB gene among the other species, to search highly conserved amino acid sequence region among various species, to synthesize PCR primers based on the nucleotide sequence of the region and to amplify serB homologue with these primers. However, since there were few such conserved regions, they estimated that it was difficult to obtain the objective gene by PCR. Therefore, complementation test utilizing serB deficient mutant strain was performed.

While the DNA of the present invention was obtained by cloning by complementation test utilizing serB deficient mutant and subcloning by PCR as described above, it can also be obtained from a chromosome DNA library of *Brevibacterium flavum* by hybridization utilizing an oligonucleotide as a probe prepared based on the nucleotide sequence of the DNA of the present invention.

Methods for construction of genomic DNA library, hybridization, PCR, preparation of plasmid DNA, digestion and ligation of DNA, transformation and the like are described in Sambrook, J., Fritsch, and E. F., Maniatis, T., Molecular Cloning, Cold Spring Harbor Laboratory Press, 1.21 (1989).

The DNA of the present invention may encode phosphoserine phosphatase including substitution, deletion, insertion, addition, or inversion of one or several amino acids at one or a plurality of positions, provided that the activity of phosphoserine phosphatase encoded thereby is not deteriorated. Although the number of "several" amino acids differs depending on the position or the type of amino acid residues in the three-dimensional structure of the protein, it may be 2 to 200, preferably 2 to 50, and more preferably 2 to 20.

Further, the DNA of the present invention may encode phosphoserine phosphatase having homology of not less than 50%, preferably not less than 60%, more preferably not less than 70%, further preferably not less than 80%, and most preferably not less than 90% with the amino acid sequence of SEQ ID NO: 2, provided that the activity of phosphoserine phosphatase encoded thereby is not deteriorated.

DNA, which encodes the substantially same protein as phosphoserine phosphatase as described above, is obtained, for example, by modifying the nucleotide sequence of phosphoserine phosphatase gene, for example, by means of the site-directed mutagenesis method so that one or more amino acid residues at a specified site of the gene involve substitution, deletion, insertion, addition, or inversion. DNA modified as described above may be obtained by the conventionally known mutation treatment. The mutation treatment includes a method for treating DNA coding for phosphoserine phosphatase in vitro, for example, with hydroxylamine, and a method for treating a microorganism, for example, a bacterium belonging to the genus *Escherichia* harboring DNA encoding phosphoserine phosphatase with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutation (mutant or variant) which naturally occurs, for example, the difference in strains, species or genera of the microorganism.

The DNA, which codes for substantially the same protein as phosphoserine phosphatase, is obtained by expressing DNA having mutation as described above in an appropriate cell, and investigating the phosphoserine phosphatase activity of an expressed product. The DNA, which codes for substantially the same protein as phosphoserine phosphatase, is also obtained by isolating DNA which is hybridizable with a primer having, for example, the nucleotide sequence comprise the nucleotide numbers of 210–1547 of the nucleotide sequence of SEQ ID NO:1, under stringent conditions, and which codes for a protein having the phosphoserine phosphatase activity, from DNA coding for phosphoserine phosphatase having mutation or from a cell harboring it. The "stringent conditions" referred to herein are conditions under which so-called specific hybrid is formed, and non-specific hybrid is not formed. It is difficult to clearly express this condition by using any numerical value. However, for example, the stringent conditions include conditions under which DNA's having high homology, for example, DNA's having homology of not less than 50% are hybridized with each other, and DNA's having homology lower than the above are not hybridized with each other. Alternatively, the stringent conditions are exemplified by conditions which comprise ordinary condition of washing in Southern hybridization, e.g., 60° C., 1×SSC, 0.1% SDS, preferably 0.1×SSC, 0.1% SDS.

DNA which has homology of not less than 60%, preferably not less than 70%, more preferably not less than 80%, and most preferably not less than 90% with the nucleotide sequence of SEQ ID NO: 1, and encodes a protein having the activity of phosphoserine phosphatase is included in the DNA of the present invention.

As a probe, a partial sequence of the nucleotide sequence of SEQ ID NO: 1 can also be used. Such a probe may be prepared by PCR using oligonucleotides produced based on the nucleotide sequence of SEQ ID NO: 1 as primers, and a DNA fragment containing the nucleotide sequence of SEQ ID NO: 1 as a template. When a DNA fragment in a length of about 300 bp is used as the probe, the conditions of washing for the hybridization consist of, for example, 50° C., 2×SSC, and 0.1% SDS.

The gene, which is hybridizable under the condition as described above, includes those having a stop codon generated in the gene, and those having no activity due to mutation of active center. However, such mutant genes can be easily removed by ligating the gene with a commercially available activity expression vector, and measuring the phosphatase activity in accordance with, for example, the method of Lewis, I. Pizer (*J. Biol. Chem.*, 238(12), 3934–3944(1963)).

It is preferred that the DNA of the present invention is ligated with vector DNA autonomously replicable in cells of *Escherichia coli* and/or coryneform bacteria to prepare recombinant DNA, and the recombinant DNA is introduced into cells of *Escherichia coli* beforehand. Such provision makes following operations easy. The vector autonomously replicable in cells of *Escherichia coli* is preferably a plasmid vector which is preferably autonomously replicable in cells of a host, including, for example, pUC19, pUC18, pBR322, pHSG299, pHSG399, pHSG398, and RSF1010.

Recombinant DNA may be prepared by utilizing transposon (WO 02/02627 International Publication Pamphlet, WO 93/18151 International Publication Pamphlet, European Patent Application Laid-open No. 0445385, Japanese Patent Application Laid-open No. 6-46867, Vertes, A. A. et al., *Mol. Microbiol.*, 11, 739–746 (1994), Bonamy, C., et al., *Mol. Microbiol.*, 14, 571–581 (1994), Vertes, A. A. et al., *Mol. Gen. Genet.*, 245, 397–405 (1994), Jagar, W. et al., *FEMS Microbiology Letters*, 126, 1–6 (1995), Japanese Patent Application Laid-open No. 7-107976, Japanese Patent Application Laid-open No. 7-327680, etc.), phage vectors, recombination of chromosomes (Experiments in Molecular Genetics, Cold Spring Harbor Laboratory Press (1972); Matsuyama, S. and Mizushima, S., *J. Bacteriol.*, 162, 1196 (1985)) and the like.

When a DNA fragment having an ability to allow a plasmid to be autonomously replicable in coryneform bacteria is inserted into these vectors, they can be used as a so-called shuttle vector autonomously replicable in both *Escherichia coli* and coryneform bacteria.

Such a shuttle vector includes the followings. Microorganisms harboring each of vectors and deposition numbers in international deposition facilities are shown in parentheses.

pHC4: *Escherichia coli* AJ12617 (FERM BP-3532)
pAJ655: *Escherichia coli* AJ11882 (FERM BP-136), *Corynebacterium glutamicum* SR8201 (ATCC 39135)
pAJ1844: *Escherichia coli* AJ11883 (FERM BP-137), *Corynebacterium glutamicum* SR8202 (ATCC 39136)
pAJ611: *Escherichia coli* AJ11884 (FERM BP-138)
pAJ3148: *Corynebacterium glutamicum* SR8203 (ATCC 39137)
pAJ440: *Bacillus subtilis* AJ11901 (FERM BP-140)

These vectors are obtainable from the deposited microorganisms as follows. Cells collected at a logarithmic growth phase were lysed by using lysozyme and SDS, followed by separation from a lysate by centrifugation at 30,000×g to obtain a supernatant to which polyethylene glycol is added, followed by fractionation and purification by means of cesium chloride-ethidium bromide equilibrium density gradient centrifugation.

*Escherichia coli* can be transformed by introducing a plasmid in accordance with, for example, a method of D. A. Morrison (Methods in Enzymology, 68, 326 (1979)) or a method in which recipient cells are treated with calcium chloride to increase permeability for DNA (Mandel, M. and Higa, A., *J. Mol. Biol.*, 53, 159 (1970)).

Introduction of plasmids to coryneform bacteria to cause transformation can be performed by the electric pulse method (Sugimoto et al., Japanese Patent Application Laid-open No. 2-207791).

The phosphoserine phosphatase can be produced by expressing the DNA of the present invention using a suitable host-vector system.

As a host for the expression of the DNA of the present invention, various prokaryotic cells including bacteria belonging to the *Corynebacterium* such as *Brevibacterium flavum*, *Escherichia coli*, *Bacillus subtilis*, various eukaryotic cells including *Saccharomyces cerevisiae*, animal cells, and plant cells can be mentioned. Among these, prokaryotic cells, in particular, *Escherichia coli* and *Bacillus subtilis* are preferred.

Since the DNA of the present invention does not have a promoter, in order to express the gene it requires that a promoter which functions in the host cell, such as lac, trp and $P_L$ is ligated to the upstream of the DNA sequence. By utilizing a vector containing a promoter as the vector, the ligation of the gene to both vector and promoter can be performed by one step. As such a vector, pMW219 containing lacZ promoter (available from Nippon gene) can be mentioned.

When the DNA is highly expressed, the plasmid containing the DNA of the present invention occasionally becomes unstably. In that case, low copy vector is preferable.

The transformation can be attained by, for example, the method in which recipient cells are treated with calcium chloride to increase permeability for DNA as reported for *Escherichia coli* K-12 strain (Mandel, M. and Higa, A., *J. Mol. Biol.*, 53, 159 (1970)), or the method utilizing introduction of DNA into competent cells produced from cells at a growth phase as reported for *Bacillus subtilis* (Duncan, C. H., Wilson, G. A., and Young, F. E., Gene, 1, 153 (1977)). It is also possible to prepare a protoplast or spheroplast of DNA recipient cell, which readily incorporates DNA, and introduce DNA into it as known for *Bacillus subtilis*, *Actinomycetes* and yeast (Changs, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B., and Fink, G. R., *Proc. Natl. Acad. Sci. USA*, 75, 1929 (1978)). Electric pulse method is also effective for coryneform bacteria (Japanese Patent Application Laid-open No. 2-207791). The method can be suitably selected from these depending on the cell to be used as the host.

The phosphoserine phosphatase can be produced by culturing cells to which the DNA of the present invention is introduced in such a manner that the DNA can be expressed as described above in a medium to produce and accumulate phosphoserine phosphatase in the culture, and collecting the phosphoserine phosphatase from the culture. The culture medium can be selected according to the host to be used.

The phosphoserine phosphatase produced as described above can be purified from a cell extract or medium as required by using a usual purification method for enzymes, for example, ion exchange chromatography, gel filtration chromatography, adsorption chromatography, solvent precipitation and the like.

Further, the DNA of present invention may be utilized for breeding L-serine producing bacteria belonging to coryneform bacteria or the like. That is, by conferring or enhancing phosphoserine phosphatase activity by introducing the DNA of present invention into bacterium in a form that the DNA can be expressed, L-serine productivity is conferred and enhanced. Moreover, enhancement of phosphoserine phosphatase activity can be also performed by amplifying copy numbers of serB homologue and modifying expression control sequence in order to enhance expression of serB homologue in chromosome of *Brevibacterium flavum*. Modification of expression control sequence in chromosomal DNA is performed by, for example, substituting strong expression control sequence such as promoter and the like for that of the operon containing serB homologue (Japanese Patent Application Laid-open No. 1-215280).

Examples of the coryneform bacterium may be used for breeding L-amino acid producing bacteria include, for example, the following wild type strains:
*Corynebacterium acetoacidophilum* ATCC 13870;
*Corynebacterium acetoglutamicum* ATCC 15806;
*Corynebacterium callunae* ATCC 15991;
*Corynebacterium glutamicum* ATCC 13032;
(*Brevibacterium divaricatum*) ATCC 14020;
(*Brevibacterium lactofermentum*) ATCC 13869;
(*Corynebacterium lilium*) ATCC 15990;
*Brevibacterium flavum* ATCC 14067;
*Corynebacterium melassecola* ATCC 17965;
*Brevibacterium saccharolyticum* ATCC 14066;
*Brevibacterium immariophilum* ATCC 14068;
*Brevibacterium roseum* ATCC 13825;
*Brevibacterium thiogenitalis* ATCC 19240;
*Microbacterium ammoniaphilum* ATCC 15354;
*Corynebacterium thermoaminogenes* AJ12340 (FERM BP-1539).

Mutant strain having resistance to azaserine or â-(2-chenyl)-DL-alanine (European Patent Publication No. 943, 687) may be also utilized for breeding L-serine producing bacteria as a starting strain.

Further, the DNA of present invention may be introduced into L-serine producing bacteria with other genes of enzyme involving L-serine biosynthesis. Such genes include the gene coding for D-3-phosphoglyceratedehyidrogenase (serA) (European Patent Publication No. 943,687), phosphoserinephosphatase (serB) and phosphoserinetransaminase (serC) (European Patent Publication No. 931,833). As serA, mutant gene coding for D-3-phosphoglyceratedehydrogenase whose feedback inhibition by L-serine is desensitized (European Patent Publication No. 943,687).

L-serine may be produced directly from sugars by culturing the microorganisms to which the DNA of the present invention is introduced in such a form that the DNA can be expressed and which have L-serine producing ability in a medium to accumulate L-serine in the midium and collecting L-serine from the medium. Further, the microorganisms to which the DNA of the present invention is introduced may be applied for a method producing L-serine utilizing L-serine precursor such as glycine and the like, so long as phosphoserine phosphatase is involved in the method.

For L-serine production using the microorganisms to which the DNA of the present invention, the following medium may be used. There can be used conventional liquid media containing carbon sources, nitrogen sources, inorganic salts, and optionally organic trace nutrients such as amino acids, vitamins, etc., if desired.

As carbon sources, it is possible to use sugars such as glucose, sucrose, fructose, galactose; saccharified starch solutions, sweet potato molasses, sugar beet molasses and hightest molasses which are including the sugars described above; organic acids such as acetic acid; alcohols such as ethanol; glycerol and the like.

As nitrogen sources, it is possible to use ammonia gas, aqueous ammonia, ammonium salts, urea, nitrates and the like. Further, organic nitrogen sources for supplemental use, for example, oil cakes, soybean hydrolysate liquids, decomposed casein, other amino acids, corn steep liquor, yeast or yeast extract, peptides such as peptone, and the like, may be used.

As inorganic ions, phosphoric ion, magnesium ion, calcium ion, iron ion, manganese ion and the like may be added optionally.

In case of using the microorganism of the present invention which requires nutrients such as amino acids for its growth, the required nutrients should be supplemented.

The microorganisms are incubated usually under aerobic conditions at pH 5 to 8 and temperature ranges of 25 to 40° C. The pH of the culture medium is controlled at a predetermined value within the above-described ranges depending on the presence or absence of inorganic or organic acids, alkaline substances, urea, calcium carbonate, ammonia gas, and the like. L-Serine can be collected from the fermentation liquid, for example, by separating and removing the cells, subjecting to ion exchange resin treatment, concentration cooling crystallization, membrane separation, and other known methods in any suitable combination. In order to remove impurities, activated carbon adsorption and recrystallization may be used for purification.

BEST MODE FOR CARRYING OUT THE INVENTION

The present invention will be more concretely explained with the reference to the following example.

<1> Preparation of *Brevibacterium flavum* Chromosomal DNA Library Using a High Copy Vector Chromosome was prepared from *Brevibacterium flavum* ATCC 14067 and partially digested into approximately 4 to 6 kb fragments with restriction enzyme Sau3AI. The obtained fragment was ligated to BamHI-digested pSAC which is a shuttle vector of *Escherichia coli* and coryneform bacteria.

pSAC4 was prepared as follows.

In order to make a vector pHSG399 for *Escherichia coli* (Takara Shuzo) autonomously replicable in coryneform bacterium cells, a replication origin of the previously obtained plasmid pHM1519 autonomously replicable in coryneform bacterium cells (Miwa, K. et al., *Agric. Biol. Chem.*, 48 (1984) 2901–2903) was introduced into the vector (Japanese Patent Laid-open No. 5-7491). Specifically, pHM1519 was digested with restriction enzymes BamHI and KpnI to obtain a gene fragment containing the replication origin, and the obtained fragment was blunt-ended by using Blunting Lit produced by Takara Shuzo, and inserted into the SalI site of pHSG399 using a SalI linker (produced by Takara Shuzo) to obtain pSAC4.

Aforementioned ligation reactant was dissolved in TE buffer and *Escherichia coli* DH5á was transformed using the solution by electroporation. The transformation solution was added with SOC medium (composition: 20 g/L Bactotrypton, 5 g/L Yeast Extract, 0.5 g/L Nacl, 10 g/L glucose), incubated at 37° C. for 1 hour, and then added with an equal volume of 2×LB medium (containing 40 mg/L chloramphenicol, composition of LB medium: 1% Trypton, 0.5% Yeast Extract, 0.1% NaCl, 0.1% glucose, pH7) and incubated at 37° C. for 2 hours. The culture medium was added with equal volume of 4×LB medium containing 40% glycerol and stored at −80° C.

The aforementioned culture medium was inoculated to LB medium and plasmids were collected from obtained cells. The plasmid DNA was precipitated with ethanol and transformed into serB deficient mutant strain ME8320 (thi, serB, zhi-1::Tn10)(obtained from national genetics institute) by electroporation method. It was confirmed that ME8320 strain could not glow on the M9 medium containing 140 mg/L vitamin $B_1$, but could glow on the same medium containing 40 mg/L L-serine.

After transformation, cells were washed, plated on the M9 agar medium containing 40 mg/L vitamin $B_1$ and chloramphenicol and incubated at 37° C. for 3 to 4 days to form colonies. Plasmids were prepared from each colony and examined these size by electophoresis. As a result remarkable deletion was found. It was considered that high expression of serB gene in the cell made plasmid unstably, thus the library should be prepared using a low copy vector again.

<2> Preparation of *Brevibacterium flavum* Chromosome DNA Library Using a Low Copy Vector and Cloning of serB Gene The chromosome was prepared from *Brevibacterium flavum* ATCC 14067 and digested with Sau3AI. The reaction was controlled to make the center of distribution to be in approximately 3 kbp or more. Approximately 200 μg of obtained digest was separated by 10 to 40% sucrose density gradient centrifugation and collected as 1 ml fractions with AUTOMATIC LIQUID CHARG-ER (ADVANTEC) and MICRO TUBE PUMP (EYELA). Sucrose density gradient centrifugation was performed with SW28 rotor (Beckman) at 10° C., 260000 rpm, for 26 hours. The fraction containing the DNA fragments that the center of distribution was in approximately 3 to 4 kbp or more was precipitated with ethanol and purified with Microcon-50 (Milipore).

The chromosomal DNA fragments obtained as described above were ligated to the low copy vector pMW219 (Nippon gene, BamHI digested and dephosphorylated). The ligation reactant was dissolved in TE buffer and transformed into *Escherichia coli* DH5á by electroporation. The transformation solution was added with SOC medium, incubated at 37° C. for 1 hour and then added with an equal volume of 2×LB medium (containing 25 mg/L kanamycin) and incubated at 37° C. for 2 hours. The culture medium was added with equal volume of 4×LB medium containing 40% glycerol and stored at −80° C.

The aforementioned culture medium was inoculated to LB medium and cultivated. Plasmids were collected from obtained cells. The plasmid DNA was precipitated with ethanol and transformed into serB-deficient mutant strain ME8320 by electroporation method. After transformation, cells were washed, plated on the M9 agar medium containing 25 mg/L vitamin $B_1$ and kanamycin and incubated at 37° C. for 3 to 4 days to form colonies. Each colony was plated on the same medium and LB medium containing 25 mg/L kanamycin. The strains that could glow on the medium were selected and plasmids were prepared from the selected strains.

In order to determine nucleotide sequence of the inserted fragment of the obtained plasmid, sequencing was started from both ends of multi-cloning site of the vector with the universal primers. The sequencing was forwarded by 300 to 400 bp. Finally approximately 5 kbp of both ends of inserted fragment were sequenced. The open reading frame was searched for determined nucleotide sequence and one ORF having homology with phosphoserine phosphatase (coded by serB gene) of other known species was found. There were several region showing homology in the ORF, however, homology between the ORF and known serB was 43% in amino acid sequence and 49.4% in nucleotide sequence for *Escherichia coli* and 36.6% in amino acid sequence and 50.9% in nucleotide sequence for *Saccharomyces cerevisiae*, respectively. Nucleotide and amino acid sequences were analyzed with the Genetyx-Mac computer program (Software Development Co., Tokyo, Japan). The homology analysis was carried out according to the method developed by Lipman and Peason (Science, 227, 1435–1441, 1985).

The nucleotide sequence of the ORF having homology with other known serB gene and the flanking regions (SEQ ID No.1), and the amino acid sequence which may be encoded by the nucleotide sequence (SEQ ID No.2) are shown in the sequence listing.

<3> Cloning of the ORF Having Homology with serB

The chromosomal DNA fragment containing the ORF and approximately 200 to 300 bp of upstream and downstream regions of the ORF was cloned and complementation test of serB deficient strain was performed to confirm that the ORF showing the homology with serB gene was certainly serB gene.

The primers having the nucleotide sequence of SEQ ID Nos: 3 and 4 were designed to obtain the desired DNA by PCR. PCR was performed using these primers and chromosommal DNA prepared from *Brevibacterium flavum* ATCC 14067 as a template. The PCR reaction was performed for 30 cycles each consisting of reaction at 98° C. for 10 sec, 55° C. for 30 sec, and 72° C. for 2 minutes, with Pyrobest DNA polymerase (TaKaRa shuzo). The amplified DNA fragment and the vector pMW219 were digested with EcoRI and SalI and ligated each other to obtain the plasmid pMW218BSB. It was confirmed that there is no error introduced by PCR by sequencing of the amplified fragment. The aforementioned ORF is inserted as reverse direction to the lacZ promoter of the vector.

pMW219BSB was introduced into ME8320 strain in the same manner as described in <2> and plated on LB medium containing 25 mg/L of kanamycin. Formed colonies were picked up by 10 strains and these were inoculated and cultured in M9 medium, however, the growth was not found.

<4> Forced Expression of the ORF Having Homology with serB

The inserted fragment in PMW219BSB was changed orientation to be placed forward direction in order to be expressed forcedly. The obtained plasmid was introduced into ME8320 strain and plated on LB medium containing 25 mg/L of kanamycin. The formed colonis were found to grow on the minimal medium.

According to the aforementioned result, it was demonstrated that the aforementioned ORF having homology with serB gene has an ability to complement serB deficiency of *Escherichia coli*. Therefore, it was confirmed that the ORF is serB homologue of *Brevibacterium flavum*.

Another ORF was found just upstream of the ORF having homology with serB gene in the cloned fragment obtained as described in aforementioned <2>. It was thought that pMW219BSB could not complement serB deficiency because these ORFs were forming operon and there was no promoter region and the like just upstream of the ORF having homology with serB gene.

What is claimed is:

1. A method of producing L-serine comprising
cultivating a bacterial cell in which phosphoserine phosphatase activity is increased by enhancing expression of a polynucleotide encoding for a protein which comprises the amino acid sequence of SEQ ID NO: 2, in a medium to produce and accumulate L-serine in the medium, and
collecting L-serine from the medium,
wherein the expression of said polynucleotide is enhanced by amplifying a copy number of said polynucleotide, or by substituting a promoter of said polynucleotide with a heterologous promoter.

2. A method of producing L-serine comprising
cultivating a bacterial cell in which phosphoserine phosphatase activity is increased by enhancing expression of a polynucleotide encoding for a protein which has phosphoserine phosphatase activity, and has homology of at least 90% to the amino acid sequence of SEQ ID NO: 2, in a medium to produce and accumulate L-serine in the medium, and
collecting L-serine from the medium,
wherein said polynucleotide is a DNA sequence which hybridizes with a DNA sequence that encodes for the amino acid sequence of SEQ ID NO: 2 under stringent conditions comprising washing at 60° C. and at a salt condition of 1×SSC and 0.1% SDS, and
wherein the expression of said polynucleotide is enhanced by amplifying a copy number of said polynucleotide, or by substituting a promoter of said polynucleotide with a heterologous promoter.

3. A method of producing L-serine comprising
cultivating a bacterial cell in which phosphoserine phosphatase activity is increased by enhancing expression of a polynucleotide which comprises nucleotides 210–1547 of SEQ ID NO: 1, in a medium to produce and accumulate L-serine in the medium, and
collecting L-serine from the medium,
wherein the expression of said polynucleotide is enhanced by amplifying a copy number of said polynucleotide, or by substituting a promoter of said polynucleotide with a heterologous promoter.

4. A method of producing L-serine comprising
cultivating a bacterial cell in which phosphoserine phosphatase activity is increased by enhancing expression of a polynucleotide encoding for a protein which has phosphoserine phosphatase activity, and has homology of at least 90% to the amino acid sequence of SEQ ID NO: 2, in a medium to produce and accumulate L-serine in the medium, and
collecting L-serine from the medium,
wherein said polynucleotide is a DNA sequence which hybridizes with a DNA sequence comprising nucleotides 210–1547 of sequence of SEQ ID NO: 1 under stringent conditions comprising washing at 60° C. and at a salt condition of 1×SSC and 0.1% SDS, and
wherein the expression of said polynucleotide is enhanced by amplifying a copy number of said polynucleotide, or by substituting a promoter of said polynucleotide with a heterologous promoter.

* * * * *

UNITED STATES PATENT AND TRADEMARK OFFICE
CERTIFICATE OF CORRECTION

| | | |
|---|---|---|
| PATENT NO. | : 7,029,896 B2 | Page 1 of 1 |
| APPLICATION NO. | : 10/321382 | |
| DATED | : April 18, 2006 | |
| INVENTOR(S) | : Mikiko Suga et al. | |

It is certified that error appears in the above-identified patent and that said Letters Patent is hereby corrected as shown below:

Column 17, line 37, "encoding for" should read --encoding-- line 49, "encoding for" should read --encoding-- line 56, "encodes for" should read --encodes--

Column 18, line 47, "encoding for" should read --encoding--

Signed and Sealed this

Twenty-second Day of August, 2006

JON W. DUDAS
*Director of the United States Patent and Trademark Office*